United States Patent [19]

Koeneman et al.

[11] Patent Number: 4,895,141

[45] Date of Patent: Jan. 23, 1990

[54] UNILATERAL EXTERNAL FIXATION DEVICE

[75] Inventors: James B. Koeneman, Mesa; Thomas M. Hansen, Phoenix; Mark Phillips, Mesa; Allan M. Weinstein, Paradise Valley, all of Ariz.

[73] Assignee: Harrington Arthritis Research Center, Phoenix, Ariz.

[21] Appl. No.: 122,397

[22] Filed: Nov. 19, 1987

Related U.S. Application Data

[63] Continuation-in-part of Ser. No. 791,222, Oct. 25, 1985, Pat. No. 4,747,400, which is a continuation-in-part of Ser. No. 604,047, Apr. 26, 1984, Pat. No. 4,584,995.

[51] Int. Cl.$^4$ ............................................. A61F 5/04
[52] U.S. Cl. ...................................... 606/54; 606/59; 606/57
[58] Field of Search ........... 128/92 Z, 92 ZZ, 92 ZY, 128/92 ZK, 92 ZW

[56] References Cited

U.S. PATENT DOCUMENTS

| | | | |
|---|---|---|---|
| 214,907 | 4/1879 | Grimmitt | 269/248 |
| 2,080,802 | 5/1937 | Anderson | 128/85 |
| 2,371,519 | 3/1945 | Haynes | 128/84 B |
| 2,398,915 | 4/1946 | Bell | 128/92 R |
| 2,434,431 | 1/1948 | Pincock | 128/92 R |
| 2,697,433 | 12/1954 | Zehnder | 128/83 |
| 3,160,448 | 12/1964 | Abernathy et al. | 384/23 |
| 3,547,113 | 12/1970 | Swanson | 128/84 R |
| 3,847,489 | 11/1974 | Van Riper | 403/110 |

(List continued on next page.)

FOREIGN PATENT DOCUMENTS

| | | | |
|---|---|---|---|
| 2532539 | 6/1976 | Fed. Rep. of Germany | 128/92 R |
| 2718515 | 11/1977 | Fed. Rep. of Germany | 128/92 R |
| 0611612 | 5/1978 | U.S.S.R. | 128/92 R |
| 0667205 | 6/1979 | U.S.S.R. | 128/92 R |
| 0770487 | 10/1980 | U.S.S.R. | 128/92 R |
| 0829105 | 5/1981 | U.S.S.R. | 128/92 R |
| 1009445 | 4/1983 | U.S.S.R. | 128/92 R |
| 1049056 | 10/1983 | U.S.S.R. | 128/92 R |
| 1149960 | 4/1985 | U.S.S.R. | 128/92 R |
| 2040168 | 8/1980 | United Kingdom | 128/92 R |
| 2086231 | 5/1982 | United Kingdom | 128/92 R |

OTHER PUBLICATIONS

Howmedica, Inc. brochure, "The External Fixation System", pp. 1–32.
E. Y. Chao et al, *J. Biomechanics*, "Rigidity and Stress Analyses of External Fracture Fixation Devices—A Theoretical Approach", vol. 15, No. 12, pp. 971–982.
E. Y. S. Chao et al, *Finite Elements in Biomechanics*, "Biomechanical Analysis of External Fixation Devices for the Treatment of Open Bone Fractures", pp. 195–220.
Mears, Dana C., "External Skeletal Fixation", pp. 1–41.
Ace Medical brochure, "The Ace-Fischer Fixator", pp. 1–12.
G. Hierholzer et al, *Manual on the AO/ASIF Tubular External Fixator*, copyright 1985, entire book, pp. 1–102.
Thackray Brochure, "Shearer External Fixation System", pp. 1–9.

*Primary Examiner*—Robert A. Hafer
*Assistant Examiner*—Kevin G. Rooney
*Attorney, Agent, or Firm*—Wood, Herron & Evans

[57] ABSTRACT

A unilateral external fixation device comprises a distal frame and a proximal frame interconnected by a hinge formed of mating, partially spherical-shaped surfaces which permits relative movement of the distal frame and proximal frame. Each of the frames includes one or more pin clamps which mount half pins inserted with the proximal or distal segments of a fractured bone to immobilize the bone segments and permit reduction of the fracture. The focal point of the partially spherical-shaped surfaces of the hinge is positioned in direct alignment with the fracture, preferably in a vertical plane passing through the fracture transverse to the longitudinal axis of the bone, so that manipulation of one or both of the distal and proximal frames permits a relatively slight and precise movement of the bone segments connected thereto by the half pins to ensure proper reduction of the fracture.

16 Claims, 3 Drawing Sheets

U.S. PATENT DOCUMENTS

| | | | |
|---|---|---|---|
| 3,866,607 | 2/1975 | Forsythe et al. | 128/92 R |
| 3,877,424 | 4/1975 | Murray | 128/92 R |
| 3,977,397 | 8/1976 | Kalnberz et al. | 128/92 R |
| 4,078,302 | 3/1978 | Fok et al. | 29/741 |
| 4,244,360 | 1/1981 | Dohogne | 128/92 R |
| 4,271,832 | 6/1981 | Evans et al. | 128/92 ZW |
| 4,299,212 | 11/1981 | Goudfrooy | 128/92 ZW |
| 4,308,863 | 1/1982 | Fischer | 128/92 R |
| 4,361,144 | 11/1982 | Slatis et al. | 128/92 R |
| 4,365,624 | 12/1982 | Jaquet | 128/92 R |
| 4,397,308 | 8/1983 | Hepburn | 128/80 F X |
| 4,488,542 | 12/1984 | Helland | 128/92 Z |
| 4,554,915 | 11/1985 | Brumfield | 128/92 Z |
| 4,582,758 | 4/1986 | Bruce et al. | 43/18.1 X |
| 4,584,995 | 4/1986 | Koeneman | 128/92 A |
| 4,620,533 | 11/1986 | Mears | 128/92 Z |
| 4,621,627 | 11/1986 | DeBastiani et al. | 128/92 ZZ |
| 4,628,919 | 12/1986 | Clyburn | 128/92 ZK |
| 4,637,382 | 1/1987 | Walker | 128/92 Z |
| 4,693,240 | 9/1987 | Evans | 128/92 Z |

UNILATERAL EXTERNAL FIXATION DEVICE

RELATED APPLICATIONS

This application is a continuation-in-part of application Ser. No. 791,222, filed Oct. 25, 1985, now U.S. Pat. No. 4,747,400 "External Fixation Device", which is a continuation-in-part of application Ser. No. 604,047, filed Apr. 26, 1984, and entitled "External Fixation Device", now U.S. Pat. No. 4,584,995.

BACKGROUND OF THE INVENTION

This invention relates generally to devices for the treatment of bone fractures in which soft tissue damage is present, and, more particularly, to a pre-assembled, unilateral external fixation device for controlled closed reduction of a bone fracture which is operable to apply controlled distraction and compression at the fracture site of the bone.

A variety of activities such as high speed travel and the widespread use of heavy machinery in industry have in recent years increased the frequency of severely compounded and infected long bone fractures, such as the femur, tibia, radius and ulna, with accompanying damage to the surrounding soft tissue. In order to properly manage the wound and prevent infection of the soft tissue, it is necessary to avoid covering the affected area except with appropriate dressings or skin grafts. Casts may not be used for the treatment of long bone fractures where soft tissue damage is present.

One early method of treatment of these cases, which is still used today, involves placing the patient in traction to completely immobilize the affected limb. As is well known, there are many problems attendant to long term confinement of a patient to a bed including necrotic pressure sores and muscle atrophy.

Another approach in the prior art for the treatment of such fractures involved the use of internal fixation devices such as bone plates which were secured directly to the bone. The problem with this method is that the fracture segments must be exposed to insert and affix the device, which increases the chance of infection of both the bone and surrounding soft tissue.

In order to limit the use of traction in the treatment of fractured bones with attendant soft tissue damage, and to avoid the use of bone plates and other internal fixation devices, research begun in the 1800's resulted in the development of external skeletal fixation devices. These devices generally comprise one or more retaining pins secured to the distal bone segment and proximal bone segment on opposite sides of the fracture, which are adjustably connected to a frame located externally of the affected limb.

One external fixation device commonly used today is the so-called Hoffmann system originally developed in the late 1930's. The Hoffmann fixation system includes two sets of self-drilling and self-tapping retaining pins, known as transfixing pins, each having a centrally located continuous thread. One set of two or three transfixing pins enters the soft tissue at one side of the fracture site, passes completely through the distal or proximal segment of the bone and then extends outwardly through the soft tissue on the opposite side. The same procedure is repeated for the other set of transfixing pins on the opposite side of the fracture. Each transfixing pin is connected at opposite ends to a frame which is adapted to permit translation and pivoting of the pins for properly aligning the distal and proximal segments. The frame is adjustable during the surgical procedure, and controlled distraction or compression may be applied post-operatively to maintain the bone segments in engagement and in alignment.

Different frame configurations have been employed for supporting the transfixing pins such as bilateral, triangular, circular and quadrilateral frames. See the discussion, for example, in Mears, Dana C. (1983) *External Skeletal Fixation*, The Williams & Wilkins, Baltimore, Chapter 1, pp. 1–41; Chao, E.Y.S., AN, K.N. (1982) Biomechanical Analysis Of External Fixation Devices For the Treatment Of Open Bone Fractures, *Finite Elements in Biomechanics*, John Wiley & Sons, Ltd. The above-described Hoffmann device, for example, employs a quadrilateral frame.

One problem with prior art external fixation devices employing bilateral, triangular, circular or quadrilateral frames involves the use of transfixing pins. As mentioned above, transfixing pins are first inserted into the soft tissue on the distal and proximal side of the fracture from one side of the injured limb. The surgeon can manipulate each transfixing pin around nerves and arteries in the soft tissue on one side of the limb until the transfixing pin contacts the bone and begins to enter the cortical bone. At that point, however, the path of the pin is fixed and no further manipulation is possible. There is a substantial risk of nerve and arterial damage as the pin passes through the bone and then into the soft tissue in a fixed path on the opposite side of the leg.

A second major problem with prior art external fixation devices, such as the Hoffmann device, is that the frame elements for supporting the transfixing pins are not preassembled but must be assembled during the surgery. An assortment of clamping elements and adjustment mechanisms forming the Hoffmann frame are provided in separate pieces and must be fitted together and then clamped to the transfixing pins during the surgical procedure. Unless a surgeon has great familiarity with a particular unassembled frame device, there may be a reluctance to employ an external fixation device at all.

One purpose of external fixation devices is to enable patients to move about and reduce the incidence of necrosis and other problems caused by confinement to bed. Many of the frame designs for securing transfixing pins, including the Hoffmann quadrilateral system and circular frames such as shown in U.S. Pat. Nos. 4,365,624 and 4,308,863, are extremely bulky and make it difficult for the patient to walk or otherwise move about. In addition, bulky metal frames often cover the fracture site and obstruct x-rays. While the transfixing pins must be firmly secured to apply the necessary force to the bone segments, it is desirable to make the frame as light as possible without obstructing the fracture site.

Another disadvantage of prior art external fixation devices is the difficulty in adjusting the position and force exerted by the retaining pins, both during and after surgery. During a surgical procedure and post-operatively, external fixation devices must be capable of adjusting the transfixing pins to vary the position of the bone segments and to control distraction and compression at the fracture site. It is often desirable to make relatively minor corrections of the position or force exerted by a set of retaining pins on one side of the fracture. However, in the Hoffmann quadrilateral fixation device and others, movement of the frame elements to adjust the position of one set of transfixing pins in any direction requires adjustment of other frame elements associated with the other set of transfixing pins. This unduly complicates post-operative adjustment procedures which further reduces the willingness of physicians to employ such devices.

Some of the problems with external fixation devices employing transfixing pins have been eliminated by unilateral fixation devices which consist of a single frame element located on one side of the injured limb having pin clamps to secure half pins mounted in the distal and proximal bone fragments. Half pins extend into only one side of the extremity and thus avoid the problem of damage to the soft tissue on the opposite side which can be caused by transfixing pins. Additionally, unilateral fixation devices are generally lighter in weight and present less of an obstruction to the affected area than other external fixation devices. Examples of unilateral external fixation devices include the "Shearer" external fixation system commercially available from Chas. F. Thackray Limited, Leeds, England and the "AO-ASIF" tubular external fixator commercially available from Synthes, Paoli, Pa.

One problem with unilateral fixation devices of the type described above is that they do not, provide the desired stability to prevent movement of the bone segments relative to one another, particularly axial rotation and transverse subluxation of the bone segments. In addition, fine or relatively slight adjustment of the position of the bone segments at the fracture is difficult with prior art unilateral fixation devices.

In a typical surgical procedure for an injury of the type described above, gross adjustment of the bone segment positions is made manually, usually by manipulating the distal bone segment. But it is desirable to make fine adjustments in the position of the segments once the fixation device is in place. Preferably, such fine adjustment is obtained by manipulating the frame or the pin clamps of the fixation device which are connected to the half pins inserted within either the proximal or distal bone segment. Unfortunately, any adjustment of the position of the bone segments obtained by moving either the frame or the pin clamps carried by the frame in prior art unilateral devices results in substantial movement of the bone segments at the fracture site. This prevents fine or precise adjustment of the position of the bone segments and can lead to incorrect anatomical alignment thereof.

SUMMARY OF THE INVENTION

It is therefore among the objectives of this invention to provide a single bar, unilateral fixation device for positioning and immobilizing the distal segment and proximal segment of a fractured bone to reduce the fracture, which provides for fine or precise adjustment of the relative position of the bone segments at the fracture, which is compact, light weight and stable, and which can accommodate fractures at the proximal, middle distal and distal portions of the bone.

These objectives are achieved in a unilateral external fixation device which comprises a distal frame and a proximal frame, both formed of light weight composite material, which carry pin clamps adapted to mount the outer end of half pins inserted within the segments of a fractured bone. The distal frame and proximal frame are formed with mating hinge elements which pivot relative to one another along an "arcuate" hinge surface, i.e., a portion of the surface of a sphere, which is defined by a radius of fixed length having its origin at approximately the center of the fracture in the bone. The fixation device is mounted to the bone so that the focal point of the arcuate hinge surface is located in a plane oriented generally perpendicularly to the longitudinal axis of the bone and passing through the center of the fracture. The configuration of the hinge elements and their location relative to the fracture permits fine or precise adjustment of the position of the bone segments relative to one another by manipulation of one or both of the frames connected to the bone segments by the half pins.

More specifically, the unilateral external fixation device of this invention includes a distal frame and proximal frame each comprising a rod portion, preferably non-cylindrical in shape, e.g., oval, or elliptical, which is either hollow or formed with a core of foam material. The wall of the rod portion, which either defines a hollow interior or encases a foam core, is formed of graphite weave cloth, or another composite material, impregnated with a matrix material such as epoxy resin. Each of the distal and proximal frames are formed with a cupped shaped hinging element connected to the rod portion having an inner, concavely arcuate surface and an outer, convexly arcuate surface. The concavely arcuate inner surface of one of the distal or proximal frames is slidable upon the convexly arcuate outer surface of the other frame to permit relative movement therebetween. A hinge cap is fitted over the exposed convexly arcuate outer surface of one of the hinge elements which mounts a bolt extending through each of the hinging elements of the frames. A nut is tightened on the bolt to secure the hinging elements to the hinge cap and to maintain the frames in a fixed position relative to one another.

The convexly arcuate outer surface of one frame upon which the concavely arcuate inner surface of the other frame articulates, forms an arcuate hinging surface in the shape of a partial sphere. The curvature of this arcuate hinging surface is preferably defined by a radius of fixed length having its origin at approximately the center of the fracture. The fixation device is positioned relative to the bone so that the focal point of the arcuate hinging surface is located in a plane passing through the fracture transverse to the longitudinal axis of the bone, at a distance spaced from the center of the fracture which is approximately equal to the length of the radius. It is presently contemplated that the length of such radius, and thus the spacing of the arcuate hinging surface from the center of the fracture, is preferably in the range of about two to four inches for patients having limbs of average size so that the fixation device is located relatively close to the injured limb in a position to securely clamp the half pins inserted in the bone segments. Depending upon the location of the wound and fracture in the injured limb, the center of the arcuate hinging elements of the distal and proximal frame portions can be positioned at any location within the plane passing through the center of the fracture, i.e., in the medial-lateral or anterior-posterior directions, to provide acceptable access to the wound for treatment. With the hinging surface of both the distal frame and proximal frame so positioned, either frame can be manipulated to obtain relatively fine or precise adjustment of the position of the bone segments for reduction of the fracture.

In a presently preferred embodiment, the structure for mounting the half pins to each of the frames comprises a pin block which is adapted to mount on the frame and clamp the smooth end of the half pins which extends outwardly from the injured limb. In a presently preferred embodiment, the pin clamps each comprise a pin block, structure for clamping the pin block to either the distal or proximal frames and pin clamping elements pivotally carried within the pin block for clamping one of the half pins inserted into a bone segment.

In one embodiment, the pin block is mounted to either the distal frame or proximal frame by a spacer insertable within a slot formed in the pin block. The spacer has an arcuate, inner end engagable with the rod section of the distal or proximal frames, and an outer end extending exteriorly of the slot in the pin block. A portion of the exterior surface of the pin block is threaded to receive a clamping cap which is formed with a hollow interior defining a cylindrical wall terminating at a bearing surface. The cylindrical wall of the clamping cap is matable with the external threads on the pin block so that the clamping cap can be tightened onto the pin block over the internal slot thereof. In the course of tightening the clamping cap onto the pin block, the bearing surface of the clamping cap engages the spacer and urges it against the rod portion of the distal or proximal frames to releasably mount the pin block thereto.

In an alternative embodiment, the spacer and clamping cap are connected by a pin. The spacer is inserted within the slot in the pin block and rotates with the clamping cap as it is tightened on the pin block until the spacer engages the rod portion of the distal or proximal frames.

The pin block is also formed with a throughbore, and a transverse bore which extends generally perpendicularly to and intersects the throughbore. A retainer carried within the transverse bore aligns with a projection extending into the throughbore which together form a seat for a ball clamp. In one embodiment, the ball clamp comprises a spherical ball having a throughbore defining an inner wall which is formed with internal threads at one end and a radially inwardly tapered portion at the opposite end. A hollow, cylindrical-shaped sleeve is inserted within the throughbore of the ball which is formed with a slotted, tapered end received within the tapered portion of the throughbore.

In order to clamp a half pin in place, the ball and sleeve are positioned within the throughbore so that the ball rests within the seat formed by the aligning projection and retainer. In one embodiment, a screw is inserted into the transverse bore and moved toward the throughbore to force the retainer against the ball clamp and retain the ball clamp within the seat. Alternatively, the screw and retainer are pinned together and inserted as a unit into the transverse bore with the retainer engaging the ball clamp. The ball clamp is pivotal within the seat to align the sleeve with the outer end of a half pin, which is then inserted through the sleeve.

In one embodiment, the half pin is secured in position relative to the pin clamp and frames by further tightening the screw within the transverse bore so that the retainer is forced against the ball clamp. In turn, the slotted end of the sleeve carried within the throughbore in the ball clamp is compressed against the pin to retain it in place. This clamps the ball clamp in a fixed position within the seat, and clamps the half pin securely within the sleeve.

In an alternative embodiment, the sleeve is eliminated and the ball clamp is formed with a throughbore of uniform diameter and a slot intersecting the throughbore. The pin is carried within the throughbore of the ball. In order to clamp the pin in place within the ball clamp, the retainer is forced against the ball clamp to at least partially collapse the ball clamp at its slot and compress the wall formed by the throughbore against the pin.

A compression distraction attachment is provided to permit movement of either the distal or proximal bone segment along the longitudinal axis of the bone after the external fixation device herein has been secured in place. This permits the attending physician to apply either compression or distraction to the bone segments for proper reduction of the fracture.

In one embodiment, the compression-distraction attachment herein comprises a clamp adapted to mount over the hinge cap which connects the hinge elements of the distal and proximal frames. The clamp is formed with a bore which rotatably receives one end of a threaded rod having a handle at the opposite end. Alternatively, the threaded rod is carried on an L-shaped clamp which is mounted to one end of the rod portion of either the distal frame or proximal frame instead of at the hinge elements of such frames. One or more internally threaded nuts are received on the threaded rod which are movable axially therealong in response to rotation of the rod. The rod extends substantially parallel to and spaced from the frames of the fixation device, and the nuts are positioned along the threaded rod so that each aligns with a pin clamp carried on the proximal and distal frames.

A transfer element interconnects the threaded rod with the distal or proximal frame portions so that axial movement of the nuts along the rod causes corresponding axial movement of the pin clamps along the frames. The transfer element comprises a pair of spaced yokes connected by a transverse cross member. Each of the yokes has an upper end formed with a bore which receives the threaded rod, and a lower end having spaced arms adapted to straddle the rod portion of the frames. The yokes are spaced relative to one another to receive the nut and pin clamp therebetween so that axial movement of the nut in response to rotation of the threaded rod is transmitted through the yokes to the pin clamps. In this manner, the pin clamps can be moved axially in either direction along the distal or proximal frames, substantially parallel to the longitudinal axis of the fractured bone, to apply controlled compression or distraction at the fracture.

DESCRIPTION OF THE DRAWINGS

The structure, operation and advantages of the presently preferred embodiment of this invention will become further apparent upon consideration of the following description taken in conjunction with the accompanying drawings, wherein.

DETAILED DESCRIPTION OF THE INVENTION

Referring now to FIGS. 1-5, the unilateral external fixation device 10 comprises a distal frame 12, a proximal frame 14 and a hinge 16 interconnecting the frames 12, 14. In this embodiment, each of the distal and proximal frames 12, 14 include an elliptical or oval rod portion 13, 15, respectively, each of which consists of a center core 18 and an outer wall 20. Preferably, the center core 18 is formed of a foam material such as the material commercially available under the trademark "Rohacell 71IG", which is a registered trademark of the Rohacell Company. In an alternative embodiment shown in FIG. 8, the center core 18 is removed defining a hollow interior 19.

The outer wall 20 of rod portions 13, 15 in both the FIG. 1-5 and FIG. 8 embodiments, is preferably graphite weave cloth, or a similar type of composite material, impregnated with an epoxy matrix material to form a strong, light weight structure. Depending upon the size and location of the injured bone, the length of the distal and/or proximal frame portions 12, 14 may be reduced by cutting or sawing the end from such frame portions 12, 14. This enables the device 10 to accommodate fractures at the proximal, middle distal and distal portions of a bone.

Figure 1:
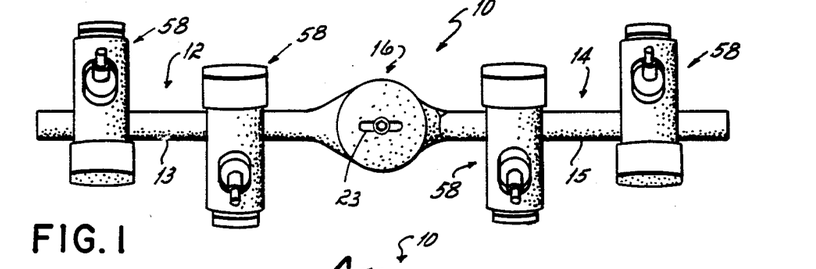
FIG. 1 is a plan view of the external fixation device of this invention.
Figures 2, 3, 4, 5:
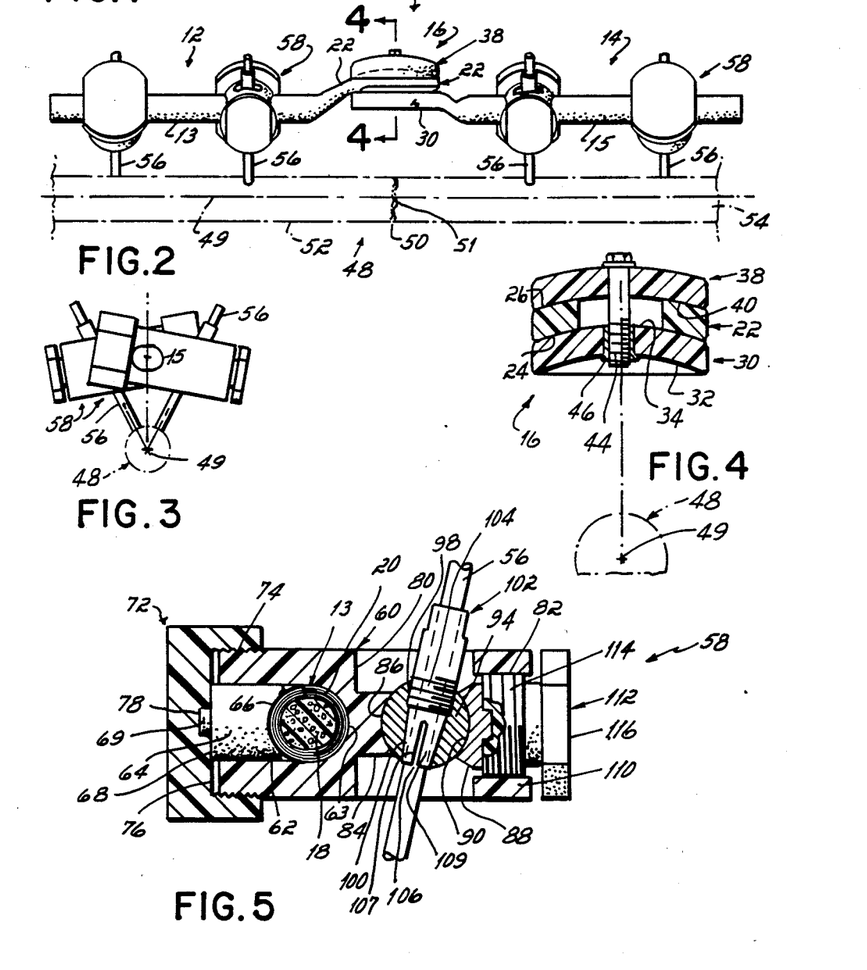
FIG. 2 is a side elevational view of the device in FIG. 1 which schematically illustrates the device in position relative to a fractured bone.
FIG. 3 is an end view of the device of Figs. 1 and 2.
FIG. 4 is a cross sectional view taken generally along line 4—4 of FIG. 2 showing the hinging elements and hinge cap of the device herein.
FIG. 5 is a partial cross sectional view of a pin clamp of this invention.

One end of the distal frame 12 is formed with a distal hinge element 22 which is angularly offset relative to the rod portion 13. The distal bearing element 22 has a generally cup-shaped cross section defining a concavely arcuate inner surface 24 and a convexly arcuate outer surface 26. A slot (not shown) extends through the inner and outer surfaces 24, 26, which preferably passes approximately through the focal point thereof. The proximal frame 14 is formed with a proximal hinge element 30 at one end of its rod portion 15 which is substantially identical to the distal hinge element 22. The proximal bearing element 30 is cup shaped in cross section defining a concavely arcuate inner surface 32 and a convexly arcuate outer surface 34 in which a slot (not shown) is formed at approximately the focal point thereof. The term "arcuate" used to describe the shape of surfaces 24, 26, 32 and 34 herein refers to a segment or portion of a spherical-shaped surface which provides the desired operation of external fixation device 10 as described in detail below.

In a presently preferred embodiment, the hinge 16 is formed by positioning the distal and proximal hinge elements 22, 30 so that the concavely arcuate inner surface 24 of the distal hinge element 22 is slidably received atop the convexly arcuate outer surface 34 of the proximal hinge element 30. See FIG. 4. The mating outer surface 34 of the proximal hinge element 30 and inner surface 24 of distal hinge element 22 permit articulation of the distal and proximal frame portions 12, 14 relative to one another for purposes described in more detail below.

The distal hinge element 22 and proximal hinge element 30 are interconnected by a hinge cap 38 having an inner concavely arcuate surface 40 which mates with the convexly arcuate outer surface 26 of the distal hinge element 22. A slot 23 is formed in the hinge cap 38 which aligns with the slots of the distal and proximal hinge elements 22, 30 respectively, to receive a bolt 44. A threaded insert 46 at the lower end of the bolt 44 is tightened to mount the hinge elements 22, 30 in a fixed position relative to one another, and to the hinge cap 38, or loosened to permit movement therebetween. In alternative embodiment (not shown), the hinge cap 38 is mounted to the proximal hinge element 30 such that the convexly arcuate surface of the hinge cap 38 mates with the concavely arcuate surface 32 of proximal hinge element 30.

Referring now to FIGS. 2 and 3, the external fixation device 10 is shown in position with respect to a bone 48 having a fracture 50 which forms a distal bone segment 52 and a proximal bone segment 54. The separate ends of the distal and proximal bone segments 52, 54 meet at the fracture 50 which has an approximate center 51 coincident with the longitudinal axis 49 of the bone 48. Although a substantially vertical fracture 50 is illustrated in FIG. 2, it is contemplated that any fracture could be accommodated by the device 10 herein and each fracture would have a "center" defined by the point coincident with the longitudinal axis of the bone where the fractured ends of the distal and proximal bone segments meet.

For purposes of illustration, two half pins 56 are inserted within each of the distal and proximal bone segments 52, 54 and extend upwardly from the bone 48 to the distal and proximal frames 12, 14. Preferably, the longitudinal axis of each half pin 56 intersects the longitudinal axis 49 of the bone 48 and forms an acute angle with respect to a vertical plane passing through the longitudinal axis 49. See FIG. 3. In many instances, the half pins 56 in each of the distal and proximal bone segments 52, 54 are preferably inserted on opposite sides of the segments for improved stability of the fixation device 10. It should be understood, however, that the half pins 56 could be positioned all on one side or the other of either bone segment 52, 54, and essentially any number of half pins 56 could be inserted in each segment 52, 54 depending upon the extent of the injury.

In the embodiment illustrated in FIGS. 1-7, the outwardly extending end of each of the half pins 56 is mounted to either the distal or proximal frames 12, 14 by a pin clamp 58. Each of the four pin clamps 58 illustrated in FIGS. 1-7 is identical and reference is made to FIG. 5 for the detailed structure of one of the pin clamps 58.

Each pin clamp 58 comprises a pin block 60 formed with a laterally extending slot 62 on one side, i.e., the left hand side as viewed in FIG. 5. The innermost end of the slot 62 is formed with an arcuate surface 63 adapted to rest against one side of the rod portions 13, 15 of the distal or proximal frames 12, 14. A spacer 64 is insertable within the slot 62, and the spacer 64 is formed with an end having an arcuate surface 66 adapted to mate with the rod portions 13, 15, and an outer end 68 having a projection 69 which extends outwardly from the slot 62. The outer surface of the pin block 60 is preferably cylindrical in shape, and a portion of such outer surface of pin block 60 at the outer end of the slot 62 is formed with external threads. A clamping cap 72 is formed with a hollow interior which defines a cylindrical wall 74 having internal threads which mate with the external threads on the outer surface of pin block 60. The cylindrical wall 74 terminates at a transverse bearing surface 76 having a recess 78 adapted to receive the projection 69 at the outer end of the spacer 64.

In order to mount the pin block 60 to either of the distal or proximal frames 12, 14, the spacer 64 is first inserted within the slot 62 so that its arcuate surface 66 contacts the rod portion 13, 15 of the distal or proximal frames 12, 14. The clamping cap 72 is then threaded onto the pin block 60 so that its transverse bearing surface 76 contacts the outer end 68 of the spacer 64. The clamping cap 72 is tightened down to force the spacer 64 against either frame 12 or 14 which secures the pin block 60 thereto. The pin blocks 60 are rotatable on the distal and proximal frames 12, 14, before tightening clamping cap 72, to vary their angular position relative to the bone 48 in order to align with the half pins 56.

The half pins 56 are clamped to the pin clamps 58 by the structure illustrated on the right hand side of the drawing in FIG. 5. The pin block 60 is formed with a vertical throughbore 80, and a transverse bore 82 which extends perpendicular to and intersects the throughbore 80. A projection 84 is formed in the pin block 60 approximately midway along the throughbore 80 having an arcuate surface 86 extending radially inwardly into the throughbore 80. A retainer 88 is carried within the transverse bore 82 having an arcuate surface 90 which extends into the throughbore 80 in alignment with the arcuate surface 86 of projection 84. These arcuate surfaces 86, 90 together form a seat which is adapted to receive a ball 94.

The ball 94 is formed with a throughbore defining an internal wall having a threaded upper portion 98 and a lower, radially inwardly tapered portion 100. The throughbore of ball 94 receives a sleeve 102 formed with a throughbore adapted to receive the outwardly extending end of a half pin 56. A portion of the outer wall of sleeve 102 is formed with external threads 104 which mate with the threaded upper portion 98 of throughbore 96, and the lower end of the sleeve 102 includes a tapered wall 108 which mates with the tapered portion 100 of the throughbore 96 in ball 94. The tapered wall 108 is formed with a slot 106 defining spaced fingers 107 and 109.

An inner wall 110 formed in the pin block 60 by transverse bore 82 is threaded to receive a screw 112 having a threaded stem 114 connected to a head 116. In order to retain the ball 94 and sleeve 102 within the throughbore 96, the screw 112 is rotated within the transverse bore 82 so that its threaded stem 114 forces the retainer 88 against the ball 94. Initially, sufficient pressure is maintained on the ball 94 to retain it within seat formed by the projection 84 and retainer 88, but permit pivotal motion of the ball 94 therein so that the sleeve 102 can be positioned in alignment with the outer end of a half pin 56. A half pin 56 is then inserted into the sleeve 102 for mounting to either the distal or proximal frame portions 12, 14.

In order to fixedly retain the half pin 56 within the ball 94 and sleeve 102, the screw 112 is rotated and moves laterally in the transverse bore 82 to force the retainer 88 tightly against the ball 94. This locks the ball 94 in position relative to the seat formed by projection 84 and retainer 88. Further tightening of the screw 112 collapses the wall of the throughbore 96 to some extent, which, in turn, forces the opposed fingers 107, 109 formed in the tapered wall 108 of the sleeve 102 inwardly against the half pin 56 to fixedly retain it in place within the pin clamp 58. The procedure is reversed to release the half pins 56.

Figure 9:
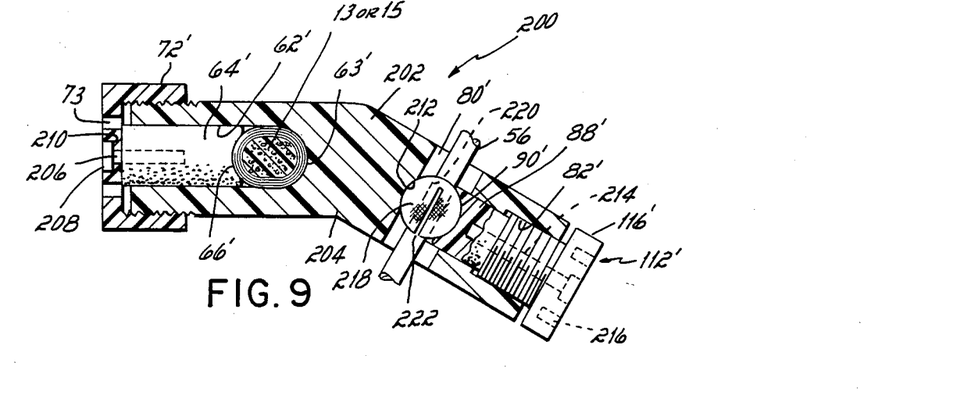
FIG. 9 is a view similar to FIG. 5 of an alternative embodiment of the pin clamp herein.

Referring now to FIG. 9, an alternative embodiment of the pin clamp for mounting the half pins 56 is illustrated. The pin clamp 200 of this embodiment is similar in many respects to pin clamp 58 described above and illustrated in FIG. 5, and therefore structural elements common to both pin clamp 58 and pin clamp 200 are given the same reference numbers with the addition of a "prime" to the reference numbers in FIG. 9.

The pin clamp 200 comprises a pin block 202 formed with a bend 204 so that the righthand portion of the pin block 202 as viewed in FIG. 9 is oriented at an acute angle of about 30° with respect to the lefthand portion of the pin block 202. The lefthand portion of pin block 202 is formed with a slot 62' having an arcuate inner surface 63' adapted to rest against one side of the rod portions 13, 15 of the distal or proximal frames 12, 14. The spacer 64' and clamping cap 72' are similar to the corresponding structure of pin clamp 58 described above, except that the projection 69 on the spacer 64 of pin clamp 58 is removed in the embodiment of FIG. 9. Instead, a pin 206 extends through the head of the clamping cap 72' and into the spacer 64' to maintain such parts in assembled relation. The head 208 of pin 206 rests within a seat 210 formed in the clamping cap 72'. In order to mount the pin clamp 200 to the rod portions 13, 15, the spacer 64' is inserted into the slot 62' an the clamping cap 72' is rotated on the threaded outer portion of pin block 202 by a spanner wrench (not shown) matable with the spaced bores 73 formed in the head of clamping cap 72'. Rotation of the clamping cap 72' forces the arcuate surface 66' of spacer 64' into contact with a rod portion 13 or 15 of the distal and proximal frames 12, 14 in the same manner as described above in connection with a discussion of pin clamp 58.

The structure for mounting a half pin 56 to the pin clamp 200 is also similar to that described above for pin clamp 58. The righthand portion of pin block 202 is formed with a throughbore 80' and a transverse bore 82' extending perpendicularly to and intersecting the throughbore 80'. An arcuate surface 212 is formed in the pin block 202 approximately midway along the throughbore 80'. A retainer 88' and screw 112' are carried within the transverse bore 82' of pin block 202 opposite the arcuate surface 212. Retainer 88' and screw 112' are substantially identical to the corresponding structure in pin clamp 58, except that a pin 214 extends therebetween to maintain retainer 88' and screw 112' in assembled relation. Additionally, the head 116' of screw 112' is formed with spaced bores 216 to receive a spanner wrench (not shown) or other specially formed tool in order to rotate the screw 112' and attached retainer 88'.

A ball 218 is insertable within the throughbore 80' and rests upon the seat formed between the arcuate surface 212 on the wall of throughbore 80' and the inwardly extending, arcuate surface 90' of the retainer 88'. The ball 218 is formed with a throughbore 220 adapted to receive a half pin 56, and a slot 222 which intersects the throughbore 220.

In order to mount a half pin 56 to the pin block 202 of pin clamp 200, the half pin 56 is inserted within the throughbore 220 of ball 218. The retainer 88' is then moved laterally inwardly, in the identical manner described in detail above with respect to a discussion of pin clamp 58, so that the ball 218 is seated between the arcuate surface 212 within the throughbore 80' and the arcuate surface 90' of retainer 88'. Further lateral movement of the retainer 88' against the ball 218 collapses a portion of the ball 218 in the area of its slot 222 to secure the half pin 56 within the pin block 202.

Figure 10:
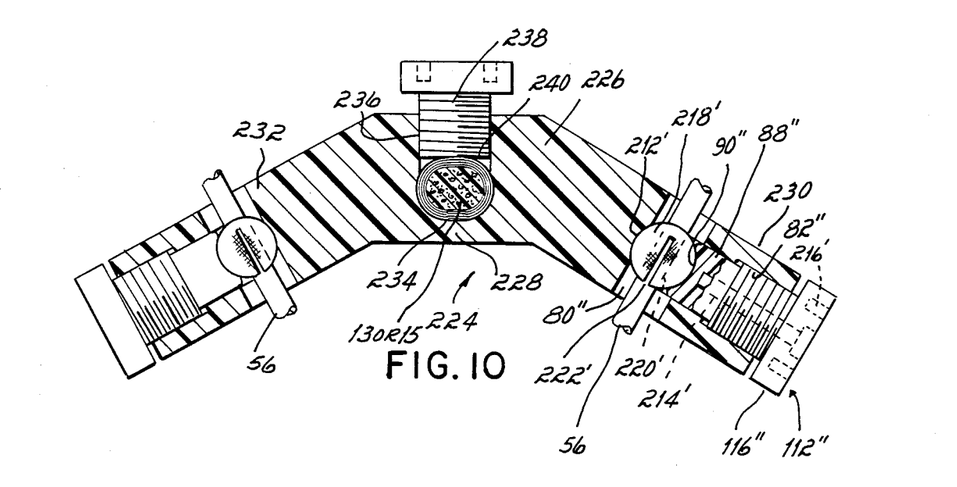
FIG. 10 is a view similar to FIGS. 5 and 9 of a still further embodiment of the pin clamp of this invention.

Referring now to FIG. 10, a pin clamp 224 is illustrated which is a still further embodiment of the pin clamps of this invention. In this embodiment, the pin clamp 224 comprises a pin block 226 having a center portion 228 and opposed end portions 230, 232 which extend outwardly at an acute angle of about 30° relative to the center portion 228. The center portion 228 is formed with an oval or elliptical-shaped bore 234 adapted to receive the rod portions 13, 15 of either the distal or proximal frames 12, 14. A screw 238 having an arcuate inner end 240 is threaded within a bore 236, which extends perpendicular to and intersects bore 234 in the center portion 228. The end 240 of screw 238 engages a rod portion 13, 15 to mount the pin block 226 thereon.

The end portions 230, 232 are identical, and thus only end portion 230 is described in detail herein. Such end portions 230, 232 are structurally similar to the right-hand portion of pin block 200 in the embodiment of FIG. 9. Structure common to FIG. 9 is given the same number in FIG. 10 with the addition of a "prime".

The end portion 230 is formed with a throughbore 80" and a transverse bore 82" which extends perpendicular to and intersects throughbore 80" The wall in end portion 230 formed by throughbore 80" has an arcuate surface 212' in alignment with the transverse bore 82". A retainer 88" identical to retainers 88, 88' of the previous embodiments, is fixedly mounted by a pin 214' to a screw 112" which is identical to screws 112, 112' of the previous embodiments. A ball 218', identical to ball 218 shown in FIG. 9 and described above, is adapted to seat between the arcuate surface 212' and the arcuate end 90" of retainer 88". The throughbore 220' formed in ball 218' is adapted to receive a half pin 56.

In order to retain the ball 218' in a fixed position within the end portion 230, and securely clamp a half pin 56 within the throughbore 220' of ball 218', the retainer 88" and screw 112" are inserted within the transverse bore 82" of end portion 230 in the identical fashion as described above in connection with retainers 88, 88' and screws 112, 112'.

The same pin clamping structure described above for end portion 230 is incorporated in end portion 232. It is contemplated that the pin clamp 224 of this embodiment would be employed where two half pins 56 must be affixed in the same area of a distal or proximal bone segment 52 or 54. One half pin 56 carried by end portion 230 would be inserted on one side of a bone segment and another half pin 56 carried by end portion 232 would be inserted on the opposite side of a bone segment at the same axial location therealong. This is an alternative arrangement to that shown in FIG. 1 wherein one half pin 56 is inserted on one side of a bone segment and carried by one pin clamp 58, and another half pin 56 carried by a second pin clamp 58 is laterally spaced from the first half pin 56 on the opposite side of the bone segment. It is contemplated that the use of pin clamps 58, 200 or 224 will be dictated by the circumstances of a particular injury and the provision of all three types of pin clamps provides the physician with greater flexibility in treating the fracture.

Figure 6:
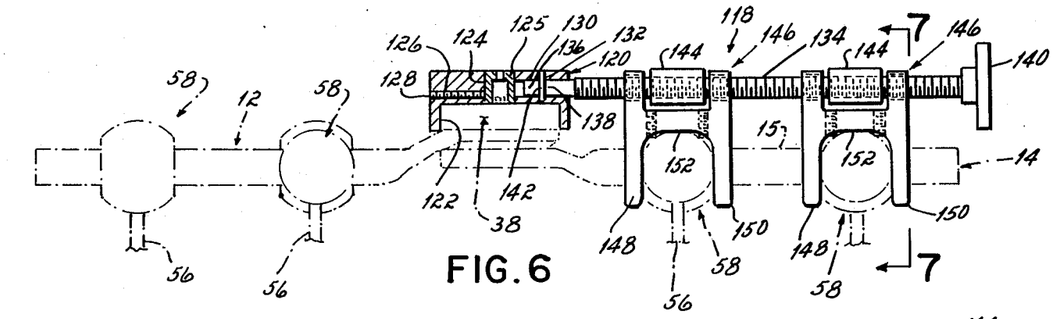
FIG. 6 is a view of the device herein similar to FIG. 2 with a compression-distraction attachment mounted thereto.
Figure 7:
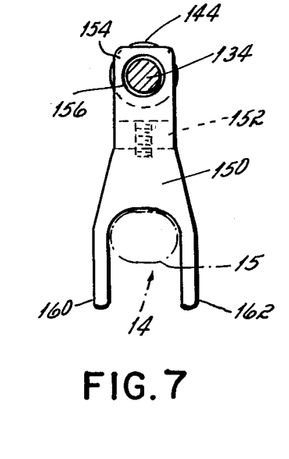
FIG. 7 is an elevational view, in partial cross section, taken generally along line 7—7 of FIG. 6.

Referring now to FIGS. 6 and 7, one embodiment of a compression-distraction attachment 118 for the external fixation device 10 is illustrated. As discussed in more detail below, the external fixation device 10 is useful in making fine or precise adjustments to the relative position of the distal bone segment 52 and proximal bone segment 54. In some instances, once the bone segments 52, 54 are properly aligned it is desirable to move them toward one another to create a compression force at the fracture 50 therebetween. In other instances, it is necessary to move one of the bone segments 52, 54 axially away from the other to distract so that the fracture therebetween may be properly reduced. The compression-distraction attachment 118 enables the physician to apply compression or distraction with the external fixation device 10 herein.

In one embodiment, the compression-distraction attachment 118 is mounted to the external fixation device 10 by a cup shaped clamp 120 having a hollow interior forming an inner surface 122 adapted to snugly fit over the outer edge of the hinge cap 38. The clamp 120 is formed with a central bore 124 which is concentric with the head of the bolt 44 extending through the hinge cap 38 with the clamp 120 positioned thereon as shown in FIG. 6. The central bore 124 receives a screw cap 125 which rests atop the hinge cap 38 concentric to the bolt 44 mounted to the hinge cap 38. An internally threaded transverse bore 126 formed in the clamp 120 intersects the central bore 124 and receives a set screw 128 which engages the screw cap 125 to help retain the clamp 120 atop the hinge cap 38. The opposite side of the clamp 120 is formed with a lateral bore 130 which is intersected by a vertically extending bore 132.

The compression-distraction attachment 118 also includes a rod 134 formed with external threads along substantially its entire length. One end 136 of the rod 134 is not threaded and is formed with an annular recess 138. The opposite end of the rod 134 mounts a handle 140. The rod 134 is mounted to the clamp 120 of compression-distraction attachment 118 by inserting its end 136 within the lateral bore 130 so that the annular recess 138 in end 136 aligns with the vertical bore 132 of clamp 120. A dowel pin 142 is then inserted within the vertical bore 132 which extends into the annular recess 138. This permits rotation of the rod 134 within the lateral bore 130 but retains the rod 134 therein.

Figure 8:
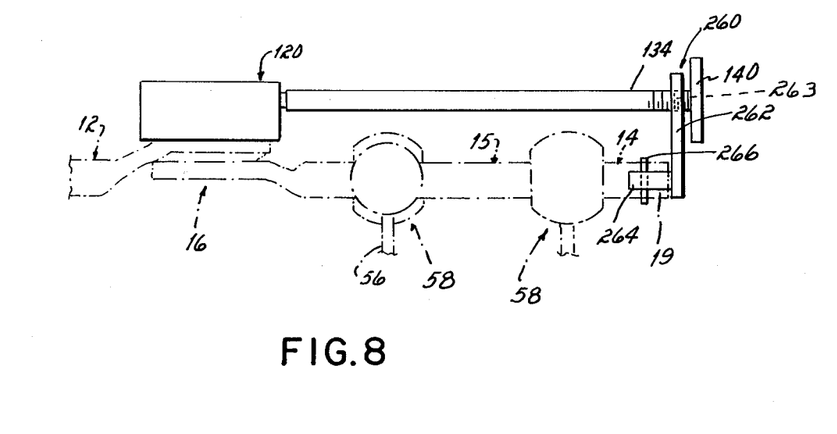
FIG. 8 is a view similar to FIG. 6 illustrating an alternative embodiment of the structure for mounting the compression-distraction attachment to the device herein.

In an alternative embodiment of FIG. 8, the compression-distraction attachment 118 is mounted to the external fixation device 10 by an L-shaped bracket 260. The bracket 260 has a vertical leg 262 formed with a threaded bore 263 engagable with one end of the threaded rod 134, and a horizontal leg 264 extending into a hollow portion 19 at one end of the rod portion 15 of proximal frame 14 where it is fixed in place by a pin 266.

As illustrated in FIG. 6, using either structure described above for mounting attachment 118 to the device 10, the rod 134 extends substantially parallel to and spaced from the proximal frame 14. It could also be positioned on the other side of the device 10 over the distal frame 12. In the illustrated embodiment of FIGS. 6 and 7, an internally threaded nut 144 is positioned on the threaded portion of the rod 134 in alignment with each pin clamp 58 carried on the distal frame portion 12. The nuts 144 are movable axially along the rod 134 in response to rotation thereof.

A bridging element 146 extends between the rod 134 and pin clamps 58 to transmit the axial motion of the nuts 144 along the rod 134 to the pin clamps 58. Each bridging element 146 comprises a pair of spaced yokes 148, 150 connected by a cross bar 152. Each yoke 148, 150 includes an upper portion 154 formed with a bore 156 which receives the rod 134. See FIG. 7. The yokes 148, 150 are spaced from one another so that their upper portions are positioned on opposite sides of a nut 144. The lower portion of each yoke 148, 150 is formed with a pair of spaced arms 160, 162 which straddle the rod portion 15 of proximal frame 14. The lower portions of each yoke 148, 150 are spaced from one another so that they extend on opposite sides of the pin clamp 58 to capture it therebetween. Axial movement of the nuts 144 in response to rotation of the rod handle 140 is therefore transmitted by the bridging elements 146 directly to the pin clamps 58. In turn, the distal or proximal bone segment 52, 54 connected by half pins 56 to the pin clamps 58 is moved axially to apply controlled compression or distraction, depending upon the direction of rotation of rod 134, to the fracture 50.

The external fixation device 10 of this invention is useful in positioning and immobilizing the distal and proximal bone segments 52, 54 of a fractured bone 48 to reduce the fracture. In a typical surgical procedure, the half pins 56 are first inserted at the desired locations in the distal and proximal bone segments 52, 54 on either side of the fracture 50. In order to mount the half pins 56 to the external fixation device 10, the device 10 is first located relative to the bone 48 so that its hinge 16 directly aligns with the fracture 50.

Preferably, the focal point of the convexly arcuate outer surface 34 of the proximal bearing element 30 is positioned approximately within a vertical plane passing through the fracture 50 transverse to the longitudinal axis of the bone 48. The size and curvature of the arcuate outer surface 34 of the proximal hinge element 30, and the mating arcuate inner surface 24 of distal hinge element 22, are defined by a radius of fixed length having its origin at the approximate center 51 of the fracture 50. Preferably, these surfaces 34, 24 are spaced from the fracture 50 at a distance approximately equal to the length of the radius. As discussed above, the "center" 51 of the fracture 50 is considered to be coincident with the longitudinal axis 49 of the bore 48 at the location where the fractured ends of the bone segments 52, 54 meet.

In a presently preferred embodiment, a radius of approximately two to four inches in length defines the curvature of the mating hinging surfaces of the proximal and distal hinge elements 22, 30, respectively. The convexly arcuate outer surface 34 of the proximal hinge element 30, and the mating concavely arcuate inner surface 24 of distal hinge element 22, are thus spaced approximately two to four inches from the center 51 of fracture 50 and their focal points are positioned to lie approximately within a vertical plane extending through the center 51 of fracture 50 transverse to the longitudinal axis 49 of the bone 48. In other words, the pivot or hinging surfaces of hinge 16 about which the distal and proximal frames 12, 14 articulate are located in direct alignment with the fracture 50 at a relatively short distance therefrom. It is contemplated that the arcuate surfaces of the hinging elements 22, 34 of frames 12, 14 could be formed with other curvatures and spaced at a different radii from the center 51 of fracture 50 to obtain the advantage of this arrangement as described in detail below, although a partially spherical-shaped arcuate surface is preferred. A radius of the length of two to four inches was chosen to minimize the size of the mating arcuate surfaces of hinging elements 22, 30, and to enable the device 10 to be positioned relatively close to the bone 48 and fracture 50 so that the half pins 56 are securely clamped at a point intermediate their outermost end and the point at which they exit the injured limb for improved stability.

With the hinge 16 positioned with respect to the fracture 50 as described above, the pin clamps 58 are located along the distal and proximal frames 12, 14 to receive and securely clamp the half pins 56. Gross adjustment of the position of the distal and proximal bone segments 52, 54 relative to one another is made by hand manipulation. Thereafter, the position of the distal bone segment 52 relative to the proximal bone segment 54, for example, is made by moving the distal frame 12 of the device 10 which, in turn, moves the distal bone segment 52 connected by half pins 56 thereto.

The concavely arcuate inner surface 24 of distal frame 12 slides along the pivot or hinging surface formed by the mating convexly arcuate outer surface 34 of proximal bearing element 30 of the bearing 16. By positioning the hinging surface of the frame portions 12, 14 relative to the fracture 50 as described above, manipulation of the distal frame portion 12 produces movement of less magnitude in the distal bone segment 52 even though the distal frame portion 12 is spaced from the distal bone segment 52 a distance equal to the length of the half pins 56 connected therebetween. This arrangement avoids substantial movement of the distal bone segment 52 upon movement of the distal frame portion 12 and allows for relatively precise or fine adjustment of the position of distal bone segment 52 for correct anatomical alignment with the proximal bone segment 54.

If desired by the attending physician, the compression-distraction attachment 118 may then be mounted upon the external fixation device 10 to provide axial movement of the distal bone segment 52 relative to the proximal bone segment 54 to apply controlled compression or distraction at the fracture 50.

While the invention has been described with reference to a preferred embodiment, it should be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An external fixation device for positioning and immobilizing the distal segment and proximal segment of a fractured bone to reduce the fracture, comprising:
   a distal frame having means for clamping half pins insertable within the distal segment of the fractured bone, said distal frame being formed with a distal hinge element having an arcuate surface;
   a proximal frame having means for clamping half pins insertable within the proximal segment of the fractured bone, said proximal frame being formed with a proximal hinge element having an arcuate surface matable with said arcuate surface of said distal hinge element of said distal frame;

means for interconnecting said distal hinge element with said proximal hinge element so that said mating arcuate surfaces thereof are movable relative to one another along a partially spherical-shaped surface defined by a radius of fixed length having an origin at approximately the center of the fracture to permit pivotal movement of said distal frame relative to said proximal frame for aligning the distal segment with the proximal segment of the fractured bone.

2. The external fixation device of claim 1 in which said distal frame and said proximal frame each include substantially non-cylindrical shaped rods formed with a non-cylindrical-shaped, central core of foam material and an outer wall of composite material.

3. The external fixation device of claim 2 in which said rods of said distal frame and proximal frame are elliptical or oval in shape.

4. The external fixation device of claim 1 in which said distal hinge element and said proximal hinge element are each substantially cup-shaped in cross section each having a convexly arcuate outer surface and a concavely arcuate inner surface, said concavely arcuate inner surface of said distal hinge element being slidable relative to said convexly arcuate outer surface of said proximal hinge element along said partially spherical-shaped surface defined by said radius of fixed length having an origin at approximately the center of the fracture to permit pivotal movement of said distal frame relative to said proximal frame.

5. The external fixation device of claim 4 in which said means for interconnecting said arcuate surface of said distal hinge element with said arcuate surface of said proximal hinge element comprises a hinge cap engagable with one of said convexly arcuate outer surface of said distal hinge element and said concavely arcuate inner surface of said proximal hinge element, a bolt insertable through said hinge cap and said distal and proximal hinge element s and a nut threadable onto said bolt for mounting said distal and proximal hinge elements in fixed relation to said cap.

6. The external fixation device of claim 1 in which said means for clamping half pins comprises:
 a pin block formed with a threaded outer surface and an internal slot for receiving a rod portion of said distal frame or said proximal frame;
 means for clamping said pin block to said distal frame or said proximal frame, comprising:
  (i) a spacer insertable within said internal slot of said pin block, said spacer being formed with a first end engagable with said rod portion of said distal or proximal frames and a second end extending exteriorly of said internal slot in said pin block;
  (ii) a clamping cap formed with a hollow interior defining a cylindrical wall terminating at a bearing surface, said cylindrical wall being formed with threads matable with said threaded outer surface of said pin block, said clamping cap being threaded onto said pin block so that said bearing surface contacts and forces said spacer against said rod portion of said proximal or distal frames to mount said pin block thereto;
 a seat formed in said pin block;
 pin clamping means movable means movable within said seat, said pin clamping means being formed with a throughbore defining a wall, said throughbore being adapted to receive a half pin;
 means mounted in said pin block for contacting said pin clamping means and urging said wall of said throughbore against the half pin to clamp the half pin in position on said distal frame or said proximal frame.

7. The external fixation device of claim 6 in which said pin block is formed with a first bore and a second bore intersecting said first bore, said second bore defining an internal wall formed with threads, said pin clamping means comprising:
 a projection mounted to said pin block within said first bore, said projection being formed with an arcuate surface facing said second bore;
 a retainer insertable within said second bore, said retainer having an arcuate surface extending into said first bore and facing said arcuate surface of said projection, said arcuate surfaces of said retainer and said projection forming a seat;
 a ball formed with a throughbore defining a cylindrical wall, a portion of said cylindrical wall being tapered radially inwardly, said ball being received within said seat and movable therein relative to said pin block;
 a hollow sleeve insertable within said throughbore of said ball, said sleeve being formed with a radially inwardly tapering slotted end portion which mates with said radially inwardly tapered portion of said cylindrical wall formed in said bore, said sleeve being adapted to receive an end of a half pin;
 a screw having a cylindrical stem connected to a head, said cylindrical stem being formed with external threads matable with said threaded second bore, said screw being threaded into said second bore so that said cylindrical stem forces said retainer against said ball, said tapered portion of said cylindrical wall of said ball being collapsed radially inwardly to clamp said slotted end portion of said sleeve against the half pin to retain the half pin within said pin block.

8. The external fixation device of claim 6 in which said pin block is formed with a threaded outer surface and an internal slot for receiving a rod portion of said distal or proximal frames, said means for clamping said pin block to said distal frame or said proximal frame comprising:
 a spacer insertable within said internal slot of said pin block, said spacer being formed with a first end engagable with said rod portion of said distal or proximal frames and a second end;
 a clamping cap formed with a hollow interior defining a cylindrical wall connected to a head portion, said head portion being fixedly mounted to said second end of said spacer, said cylindrical wall being formed with threads matable with said outer threaded surface of said pin block, said spacer being inserted within said internal slot and said clamping cap being threaded onto said pin block so that said first end of said spacer contacts said rod portion to mount said pin block onto said distal or proximal frame.

9. An external fixation device for positioning and immobilizing the distal segment and proximal segment of a fractured bone to reduce the fracture, comprising:

a distal frame having means for clamping half pins insertable within the distal segment of the fractured bone, said distal frame being formed with a distal hinge element having an arcuate surface;

a proximal frame having means for clamping half pins insertable within the proximal segment of the fractured bone, said proximal frame being formed with a proximal hinge element having an arcuate surface matable with said arcuate surface of said distal hinge element of said distal frame portion;

means for interconnecting said distal hinge element with said proximal hinge element so that said mating surfaces thereof are movable relative to one another along a partially spherical-shaped surface defined by a radius of fixed length having an origin at approximately the center of the fracture to permit pivotal movement of said distal frame relative to said proximal frame for aligning the distal segment with the proximal segment of the fractured bone;

compression-distraction means engagable with said pin clamp means of at least one of said distal and proximal frames for axially moving said pin clamp means relative to the longitudinal axis of the fractured bone, said pin clamp means axially moving one of the distal and proximal bone segments of the fractured bone connected thereto by half pins relative to the other of the distal and proximal bone segments.

10. The external fixation device of claim 9 in which said compression-distraction means comprises:

a threaded rod rotatably carried by said means for interconnecting said arcuate surface of said distal hinge element with said arcuate surface of said proximal hinge element;

a nut having internal threads matable with said threaded rod, said nut being movable axially along said threaded rod in response to rotation of said threaded rod;

yoke means interconnecting said nut with said pin clamp means of one of said distal and proximal frame portions, said nut contacting and moving said yoke means axially along said threaded rod, said yoke means in turn axially moving said pin clamp means and the distal or proximal bone segment connected to said pin clamp means by half pins.

11. The external fixation device of claim 10 in which said yoke means comprises a pair of spaced yoke elements connected by a leg member, each of said yoke elements having an upper end formed with a bore adapted to receive said threaded rod and a lower end formed with spaced arms adapted to straddle said distal or proximal frame portion, said yoke elements being spaced to capture said nut between said upper ends thereof and said pin clamping means between said lower ends thereof.

12. The external fixation device of claim 10 in which said distal frame and said proximal frame each include a rod portion connected to said distal hinge element and said proximal hinge element, respectively, said threaded rod being connected to one of said rod portions for mounting said compression-distraction means.

13. A method of positioning and immobilizing the distal segment and proximal segment of a fractured bone to reduce the fracture, comprising:

clamping one end of a half pin inserted within the distal segment of the fractured bone to a pin clamp carried by a distal frame of an external fixation device, said distal frame being formed with a distal hinge element having an arcuate surface;

clamping one end of a half pin inserted within the proximal segment of the fractured bone to a pin clamp carried by a proximal frame of said external fixation device, said proximal frame being formed with a proximal hinge element having an arcuated surface which mates with said arcuate surface of said distal hinge element for permitting pivotal movement therebetween;

positioning said distal hinge element and said proximal hinge element relative to the fracture so that said arcuate surface of said distal hinge element and said mating arcuate surface of said proximal hinge element pivot with respect to one another about a partially spherical-shaped surface defined by a radius of fixed length having its origin at the approximate center of the fracture of the bone so as to permit precise adjustment of the position of the distal segment at the fracture for alignment with the proximal segment.

14. The method of claim 13 in which said step of positioning said distal hinge element and said proximal hinge element comprises spacing said mating arcuate surfaces of said distal hinge element and said proximal hinge element at a distance from the center of the fracture of the bone which is approximately equal to the length of the radius having its origin at the center of the fracture.

15. The method of claim 13 in which said step of positioning said distal hinge element and said proximal hinge element comprises spacing said mating arcuate surfaces of said distal hinge element and said proximal hinge element at a distance from the center of the fracture of the bone in the range of about two inches to four inches.

16. The method of claim 13 in which said step of positioning said distal hinge element and said proximal hinge element comprises positioning the focal point of said arcuate surface of one of said distal hinge element and said proximal hinge element substantially coincident with a vertical plane extending through the center of the fracture of the bone transverse to the longitudinal axis of the bone.

* * * * *